United States Patent
Tokarski et al.

(10) Patent No.: US 7,074,532 B2
(45) Date of Patent: *Jul. 11, 2006

(54) LINKED DIHYDRAZONE-BASED CHARGE TRANSPORT COMPOUNDS

(75) Inventors: Zbigniew Tokarski, Woodbury, MN (US); Nusrallah Jubran, St. Paul, MN (US); Vytautas Getautis, Kaunas (LT); Maryte Daskeviciene, Jonava (LT); Vygintas Jankauskas, Vilnius (LT); Janina Gavutiene, Vilnius (LT)

(73) Assignee: Samsung Electronics, Co., Ltd., Suwon (KR)

( * ) Notice: Subject to any disclaimer, the term of this patent is extended or adjusted under 35 U.S.C. 154(b) by 146 days.

This patent is subject to a terminal disclaimer.

(21) Appl. No.: 10/663,278

(22) Filed: Sep. 16, 2003

(65) Prior Publication Data

US 2005/0058916 A1    Mar. 17, 2005

(51) Int. Cl.
*G03G 5/05*    (2006.01)

(52) U.S. Cl. .............................. 430/58.15; 430/58.45; 430/126; 548/138

(58) Field of Classification Search ............ 430/58.15, 430/126, 58.45, 77; 548/138
See application file for complete search history.

(56) References Cited

U.S. PATENT DOCUMENTS

| | | | |
|---|---|---|---|
| 4,297,426 A | 10/1981 | Sakai et al. | |
| 4,786,571 A | 11/1988 | Ueda | |
| 4,957,838 A | 9/1990 | Aruga et al. | |
| 5,128,227 A | 7/1992 | Monbaliu et al. | |
| 6,066,426 A | 5/2000 | Mott et al. | |
| 6,099,996 A | 8/2000 | Yanus et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,670,085 B1 | 12/2003 | Jubran et al. | |
| 6,899,984 B1 * | 5/2005 | Tokarski et al. | 430/58.45 |
| 2003/0104294 A1 | 6/2003 | Law et al. | |
| 2003/0113132 A1 | 6/2003 | Law et al. | |
| 2003/0113643 A1 | 6/2003 | Law et al. | |
| 2003/0113644 A1 | 6/2003 | Law et al. | |
| 2003/0138712 A1 | 7/2003 | Law et al. | |
| 2003/0198880 A1 | 10/2003 | Law et al. | |
| 2003/0219662 A1 | 11/2003 | Jubran et al. | |

FOREIGN PATENT DOCUMENTS

JP    62116943    5/1987

* cited by examiner

*Primary Examiner*—John L Goodrow
(74) *Attorney, Agent, or Firm*—Patterson, Thuente, Skaar & Christensen, P.A.

(57) ABSTRACT

Improved organophotoreceptors comprise:
(a) a charge transport compound having the formula

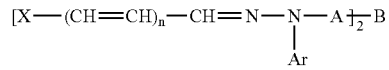

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group;
(b) a charge generating compound; and
(c) an electrically conductive substrate over which said charge transport compound and said charge generating compound are located.

18 Claims, No Drawings

LINKED DIHYDRAZONE-BASED CHARGE TRANSPORT COMPOUNDS

FIELD OF THE INVENTION

This invention relates to organophotoreceptors suitable for use in electrophotography and, more specifically, to organophotoreceptors having a charge transport compound comprising two hydrazone groups and a linking group comprising a heterocyclic group.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas. A liquid or solid toner is then deposited in either the charged or uncharged areas depending on the properties of the toner to create a toned image on the surface of the photoconductive layer. The resulting toned image can be transferred to a suitable receiving surface such as paper. The imaging process can be repeated many times to complete a single image and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport compound is to accept at least one type of these charge carriers, generally holes, and transport them through the charge transport layer in order to facilitate discharge of a surface charge on the photoconductive element.

SUMMARY OF THE INVENTION

In a first aspect, the invention features an organophotoreceptor that comprises:
(a) a charge transport compound having the formula

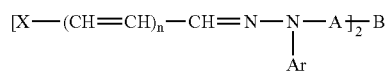

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group;
(b) a charge generating compound; and
(c) an electrically conductive substrate over which the charge transport compound and the charge generating compound are located.

In a second aspect, the invention features an electrophotographic imaging apparatus that includes (a) a plurality of support rollers; and (b) the above-described organophotoreceptor operably coupled to the support rollers with motion of the support rollers resulting in motion of the organophotoreceptor. The apparatus can further comprise a liquid or solid toner dispenser.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a toner to create a toned image; and (d) transferring the toned image to a substrate.

In a fourth aspect, the invention features charge transport compound having the formula

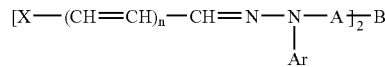

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group.

These charge transport compounds can further be used in the formation of organophotoreceptors as well as corresponding electrophotographic imaging apparatuses and electrophotographic imaging processes.

These photoreceptors can be used successfully with liquid toners to produce high quality images. The high quality of the images can be maintained after repeated cycling.

Other features and advantages of the invention will be apparent from the following description of the preferred embodiments thereof, and from the claims.

Herein, ranges of integer values include the end points of the range as possible values.

DETAILED DESCRIPTION OF PREFERRED EMBODIMENTS

Charge transport compounds with desirable properties can be formed having two linked hydrazone groups with the linkage comprising a heterocyclic group. These charge transport compounds have desirable properties as evidenced by their performance in organophotoreceptors for electrophotography. In particular, the charge transport compounds of this invention have high charge carrier mobilities and good compatibility with various binder materials; can be cross-linked in both the single and multilayer photoconductive elements; and possess excellent electrophotographic properties. The organophotoreceptor according to this invention has a high photosensitivity, a low residual potential, and high stabilities with respect to cycle testing, crystallization, and organophotoreceptor bending and stretching. The organophotoreceptors are particularly useful in laser printers and the like as well as photocopiers, scanners and other electronic devices based on electrophotography. The use of these charge transport compounds is described in more detail below in the context of laser printer use, although their application in other devices operating by electrophotography can be generalized from the discussion below.

To produce high quality images, particularly after multiple cycles, it is desirable for the charge transport compounds to form a homogeneous solution with the polymeric binder and remain approximately homogeneously distributed through the organophotoreceptor material during the cycling of the material. In addition, it is desirable to increase the amount of charge that the charge transport compound can accept (indicated by a parameter known as the acceptance voltage or "$V_{acc}$"), and to reduce retention of that charge upon discharge (indicated by a parameter known as the discharge voltage or "$V_{dis}$").

There are many charge transport compounds available for electrophotography. Examples of charge transport compounds are pyrazoline derivatives, fluorene derivatives, oxadiazole derivatives, stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of triphenylamine and heterocycles such as carbazole, julolidine, phenothiazine, phenazine, phenoxazine, phenoxathiin, thiazole, oxazole, isoxazole, dibenzo (1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline. Charge transport compounds comprising a dihydrazone-based compound with an aryl linking group is described further in copending U.S. patent application Ser. No. 10/431,138 to Tokarski et al., entitled "Linked Dihydrazone-Based Charge Transport Compounds," incorporated herein by reference. However, there is a need for other charge transport compounds to meet the various requirements of particular electrophotography applications.

In electrophotography applications, a charge generating compound within an organophotoreceptor absorbs light to form electron-hole pairs. These electron-hole pairs can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compounds described herein are especially effective at transporting charge, and in particular holes from the electron-hole pairs formed by the charge generating compound. In some embodiments, a specific electron transport compound can also be used along with the charge transport compound.

The layer or layers of materials containing the charge generating compound and the charge transport compounds are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport compound can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport compound and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toned image, to attract toner to the charged or discharged regions of the organophotoreceptor; and (d) transferring the toned image to a substrate.

This invention features an organophotoreceptor that includes a charge transport compound having the formula

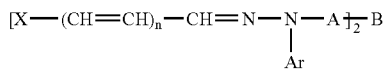

where n is an integer from 0 to 1;

X is an (N,N-disubstituted)arylamine group, such as a carbazole group, a julolidine group, or a p-(N,N-disubstituted)arylamine group (which can be a triarylamine, an alkyldiarylamine or a dialkylarylamine);

Ar is an aryl group or a heterocyclic group;

A is a first linking group with the formula $-(CH_2)_p-$ which can be branched or linear, where p is an integer from 3 to 20 inclusive and where one or more methylene groups can be optionally replaced by O, S, a carbonyl group, urethane, urea, an ester group, a $-NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group.

In describing chemicals by structural formulae and group definitions, certain terms are used in a nomenclature format that is chemically acceptable. The terms groups and moiety have particular meanings. The term group indicates that the generically recited chemical entity (e.g., alkyl group, phenyl group, julolidine group, (N,N-disubstituted) arylamine group, etc.) may have any substituent thereon which is consistent with the bond structure of that group. For example, alkyl group includes alkyl materials such as methyl ethyl, propyl iso-octyl, dodecyl and the like, and also includes such substituted alkyls such as chloromethyl, dibromoethyl, 1,3-dicyanopropyl, 1,3,5-trihydroxyhexyl, 1,3,5-trifluorocyclohexyl, 1-methoxy-dodecyl, phenylpropyl and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, ortho-cyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical material is not substituted.

Organophotoreceptors

The organophotoreceptor may be, for example, in the form of a plate, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate, a photoconductive element in the form of one or more layers. In general, layers of the photoconductive element may be formed in accordance with any appropriate technique known in the art, such as dip coating, spray coating, extrusion, and the like. The photoconductive element can comprise both a charge transport compound and a charge generating compound in a polymeric binder, which may or may not be in the same layer, as well as an electron transport compound in some embodiments. For example, in some embodiments with a single layer construction, the charge transport compound and the charge generating compound are in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodide, conductive polymers such as polypyroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material which is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound, e.g., ELA 7051 oxytitanyl phthalocyanine available from H.W. Sands, Inc.), hydroxygallium phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may contain an electron transport compound. Generally, any electron transport compound known in the art can be used. Non-limiting examples of suitable electron transport compound include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene) thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene) malononitrile, and diethyl(4-n-butoxy carbonyl-2,7-dinitro-9-fluorenylidene)malonate, anthraquinodimethane derivatives such as 11,11,12,12-tetracyano-2-alkylanthraquinodimethane and 11,11-dicyano-12,12-bis(ethoxycarbonyl) anthraquinodimethane, anthrone derivatives such as 1-chloro-10-[bis(ethoxycarbonyl)methylene]anthrone, 1,8-dichloro-10-[bis(ethoxycarbonyl)methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene)malononitrile.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. While not wanting to be limited by theory, the synergistic relationship contributed by the UV stabilizers may be related to the electronic properties of the compounds, which contribute to the UV stabilizing function, by further contributing to the establishment of electron conduction pathways in combination with the electron transport compounds. In particular, the organophotoreceptors with a combination of the electron transport compound and the UV stabilizer can demonstrate a more stable acceptance voltage $V_{acc}$ with cycling. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

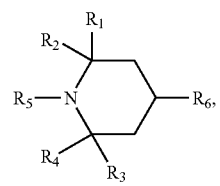

-continued

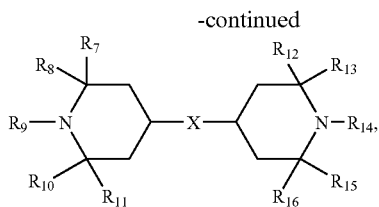

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independently, hydrogen, alkyl group, or ester, or ether group; and $R_5$, $R_9$, and $R_{14}$ are, independently, alkyl group; and X is a linking group selected from the group consisting of —O—CO—$(CH_2)_m$—CO—O— where m is between 2 to 20.

The binder generally is capable of dispersing or dissolving the charge transport compound (in the case of the charge transport layer or a single layer construction) and/or the charge generating compound (in the case of the charge generating layer or a single layer construction). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. In some embodiments, the binder is selected from the group consisting of polycarbonates, polyvinyl butyral, and a combination thereof. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates. Suitable binders with reactive functionality include, for example, polyvinyl butyral, such as BX-1 and BX-5 form Sekisui Chemical Co. Ltd., Japan.

Suitable optional additives for any one or more of the layers include, for example, antioxidants, coupling agents, dispersing agents, curing agents, surfactants, and combinations thereof.

The photoconductive element overall typically has a thickness from about 10 to about 45 microns. In the dual layer embodiments having a separate charge generating layer and a separate charge transport layer, charge generation layer generally has a thickness from about 0.5 to about 2 microns, and the charge transport layer has a thickness from about 5 to about 35 microns. In embodiments in which the charge transport compound and the charge generating compound are in the same layer, the layer with the charge generating compound and the charge transport composition generally has a thickness from about 7 to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent in further embodiments in an amount from about 1 to about 15 weight percent and in other embodiments in an amount from about 2 to about 10 weight percent, based on the weight of the photoconductive layer. The charge transport compound is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional electron transport compound, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional electron transport compound in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of the compositions for the dual layer embodiments within the explicit ranges above are contemplated and are within the present disclosure.

For the embodiments with a single layer having a charge generating compound and a charge transport compound, the photoconductive layer generally comprises a binder, a charge transport compound, and a charge generation compound. The charge generation compound can be in an amount from about 0.05 to about 25 weight percent and in further embodiment in an amount from about 2 to about 15 weight percent, based on the weight of the photoconductive layer. The charge transport compound can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport compound may comprise an electron transport compound. The optional electron transport compound, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in a copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any of one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, a charge transport compound, an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer forms the uppermost layer of the photoconductor element. A barrier layer may be sandwiched between the release layer and the photoconductive element or used to overcoat the photoconductive element. The barrier layer provides protection from abrasion and/or carrier liquid to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/ vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

The overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound as described above may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport compounds as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. patent application Ser. No. 2002/0128349, entitled "Liquid Inks Comprising A Stable Organosol," U.S. patent application Ser. No. 2002/0086916, entitled "Liquid Inks Comprising Treated Colorant Particles," and U.S. patent application Ser. No. 2002/0197552, entitled "Phase Change Developer For Liquid Electrophotography," all three of which are incorporated herein by reference.

Charge Transport Compound

In some embodiments, the organophotoreceptors as described herein can comprise a two hydrazone based compound as a charge transport compound having the formula

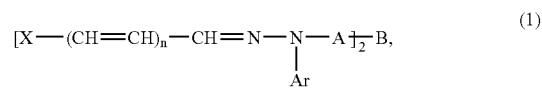

where n is an integer from 0 to 1; X is an (N,N-disubstituted) arylamine group, such as a carbazole group, a julolidine group, or a p-(N,N-disubstituted)arylamine group (which can be a triarylamine, an alkyldiarylamine or a dialkylarylamine); Ar is an aryl group or a heterocyclic group; A is a first linking group; and B is a second linking group. The first linking group A has the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring. The second linking group B has the formula -Q-Z-Q'-, where Q and Q' are, independently, O, S, or $NR_1$, where $R_1$ is an H, an alkyl group, an alkaryl group or an aryl group and Z comprises a heterocyclic group.

Non-limiting examples of the charge transport compound of this invention have the following formulas:

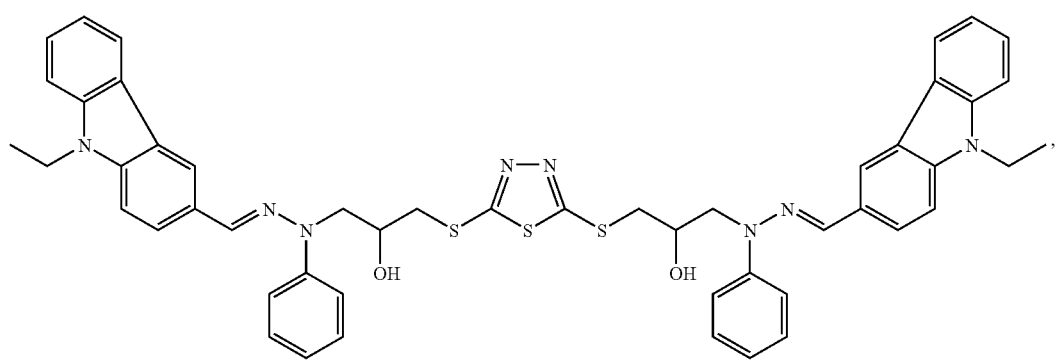

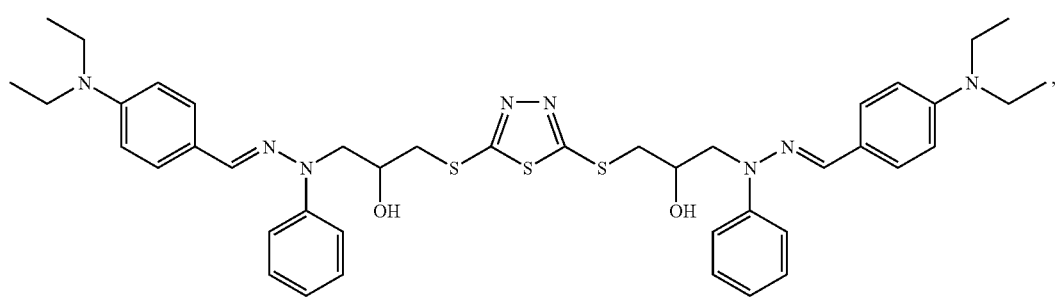

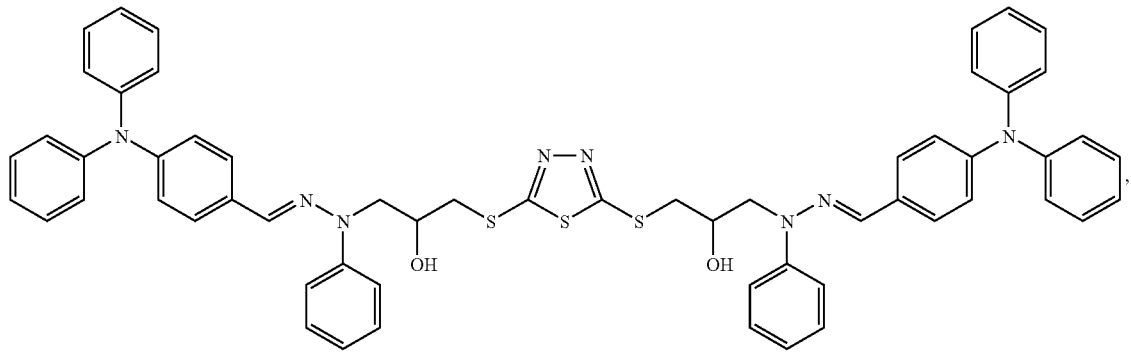

(4)

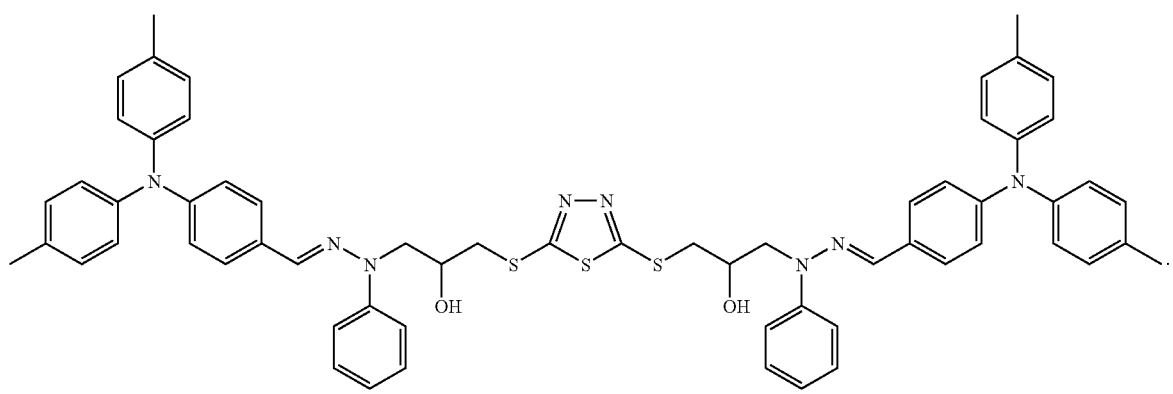

(5)

Synthesis of Charge Transport Compounds

The charge transport compounds with two linked hydrazones are based on the reaction of an aminoarylhydrazone compound with a first linker to derivatize the hydrazone and on the reaction of the derivatized hydrazone with a second linker that joins the two hydrazones. The first linker generally comprises a halogen functional group and a second functional group bonds with a functional group with active hydrogens. The second linker comprising two functional groups, with each generally having active hydrogens. The second linker connects the two hydrazones by way of the first linker.

The aminoaryl hydrazone can be formed from the reaction of an aminoaryl aldehyde or aminoaryl ketone with an aryl hydrazine. The aminoaryl hydrazone can react with the halogen functional group of the first linker to add the linker onto the aminoaryl hydrazone at the single bonded nitrogen of the hydrazone. The aminoaryl hydrazone bonded to the first linker can be referred to as a derivatized hydrazone. The first linker generally has a second functional group suitable for reaction with a functional group with active hydrogens such that the derivatized aminoaryl hydrazone is formed when the aminoaryl hydrazone bonds with the first linker.

In summary, an aminoaryl hydrazone can be formed by reacting an aminoaryl aldehyde or aminoaryl ketone with an aryl hydrazine. The aminoaryl hydrazone can be reacted with a first linker to form a derivatized hydrazone. The derivatized hydrazone can be reacted with the second linker to form the charge transport compound.

With respect to appropriate aryl hydrazines, phenylhydrazine and benzylhydrazine hydrochloride are commercially available from Aldrich (Milwaukee, Wis.). Heterocyclic aryl groups can be provided through the use of other hydrazines, such as 2-hydrazinopyridine (Aldrich) or 2-hydrazinopyrimidine (Interchim, France). Other aryl hydrazines can be formed based on derivatives the commercially available compounds or by other hydrazine derivatized aromatic compounds synthesized by appropriate approaches including those known in the art.

With respect to representative aminoaryl aldehydes, 4-(diphenylamino)benzaldehyde, 4-(diethylamino)benzaldehyde and 9-ethyl-3-carbazolcarboxyaldehyde are utilized in the Examples below and are available commercially from Aldrich, Milwaukee, Wis. Also, 4-(4,4'-dimethyldiphenylamino)benzaldehyde is used in the Examples below and is available from Synthon Chemicals GmbH & Co. KG, Germany.

In addition, julolidine aldehyde can be synthesized from julolidine, which also is available commercially from Aldrich, Milwaukee, Wis. Specifically, julolidine (10 g, 0.6 moles) can be dissolved in 200 ml warm N,N-dimethylformamide (DMF, commercially obtained from Aldrich) in a 500 ml three neck round bottom flask. After the julolidene is dissolved, the flask is cooled to 0° C. in an ice bath. Then, $POCl_3$ (107 g, 0.7 mole; commercially available from Aldrich) can be added drop wise via a dropping funnel while keeping the temperature below 5° C. After the addition of $POCl_3$ is completed, the flask is warmed to room temperature and placed in a steam bath where it is stirred for a period of 1 hour. The flask is cooled to room temperature and the solution is added slowly, with good agitation, to a large excess of distilled water. Stirring is continued for an additional 2 hours. The solid julolidine aldehyde is filtered off and washed repeatedly with water until the pH of the effluent water becomes neutral. The product can be dried at 50° C. in a vacuum oven for 4 hours.

For embodiments of the charge transport compound formula described above in which n=1 and X=p-dimethylaminophenyl group, p-dimethylaminocinnamaldehyde (commercially available from Aldrich) is used in place of p-dimethylaminophenylaldehyde. For n=1 and X=a carbazole group, 9-ethyl-3-carbazolecinnamaldehyde is used instead of 9-ethyl-3-carbazolecaboxaldehyde. For n=1 and X=triphenylamine, 4-(diphenylamino) cinnamaldehyde is used instead of 4-(diphenylamino)benzaldehyde. For n=1 and X=julolidine, julolidinecinnamaldehyde is used instead of julolidinealdehyde. Other aryl aldehydes for the formation of charge transport compounds with n=1 can be similarly selected. All other reactions are similar and described below. The synthesis of 9-ethyl-3-carbazolecinnamaldehyde, 4-(diphenylamino)cinnamaldehyde and julolidinecinnamaldehyde can be carried out by analogy with the commercial synthesis approach for p-dimethylaminocinnamaldehyde.

Having obtained a selected hydrazine and aryl aldehyde/ketone, the hydrazones can be synthesized from the reaction of the selected hydrazine with the aryl aldehyde/ketone in an alkaline catalyzed reaction. In some embodiments, the hydrazines are obtained in an acidified hydrochloride form. For these embodiments, the hydrazine hydrochloride can be reacted with an aqueous carbonate base and stirring of the mixture. An excess of carbonate base can be added, such as 1.2 moles of potassium carbonate for embodiments with one mole of hydrazine hydrochloride per mole hydrazine or 2.4 moles of potassium carbonate for embodiments with one mole of hydrazine dihydrochloride per mole hydrazine.

With respect to the first linker, noted as "A" following binding, the linker compound can comprise a halide group, such as Cl, for binding with the single bonded nitrogen of the hydrazone, and a second functional group for bonding with a thiol group of the second linker, noted as "B" following bonding. The second functional group of the first linker can be for example, an epoxy/oxirane group that reacts with a functional group with active hydrogens to form a secondary alcohol, a halide group reacts with an active hydrogen to form an ether, an amine or thioether, or a carbonyl halide or acid anhydride group to form an ester, an amide or a thiol carbonyl (R—SCO—R') group, as appropriate for the active hydrogen group. Additional suitable reactions involving active hydrogen groups can be used with appropriate functional groups on the first linker.

In the examples below, the second linker is a heterocyclic dimercapto compound. Specifically, the second linker was 2,5-dimercapto 1,3,4 thiadiazole (commercially available from Aldrich). Other possible heterocyclic dimercapto compounds for use as second include, for example, 2,6-dimercaptopurine (from Aldrich), 2,8-dimercaptohypoxanthine (from Chemos GmbH, Germany), 2,8-dimercapto-6-hydroxypurine from (ABCR GmbH & Co. KG, Germany), and purine-4,6-dithiol (from Connecting GmbH, Switzerland). Heterocyclic dihydroxy compounds suitable as second linkers include, for example, 6,7-dihydroxycoumarin, 2,4-dihydroxy-5,6-dimethylpyrimidine, 4,6-dihydroxy-2,5-diphenyl pyrimidine, 4,6-dihydroxy-5-ethylpyrimidine, 5,7-dihydroxyflavone, 5,7-dihydroxy-4'-methoxyisoflavone, 5,7-dihydroxy-4-methyl coumarin, 6,7-dihydroxy-4-methylcoumarin, 4,6-dihydroxy-2-methylmercaptopyrimidine, 2,6-dihydroxy-4-methyl-3-pyridinecarbonitrile, 2,4-dihydroxy-6-methylpyrimidine, 4,6-dihydroxy-2-methylpyrimidine, 4,6-dihydroxy-5-nitropyrimidine, 4,7-dihydroxy-1,10-phenantroline, 3,6-dihydroxypyridazine, 2,3-dihydroxypyridine, 2,4-dihydroxypyridine, 4,6-dihydroxypyrimidine, 2,3-dihydroxy quinoxaline (all commercially from Aldrich), 6,7-dhydroxy-3,4-dihydroisoquinoline (from Acros Organics, Janssen Pharmaceuticalaan 3a, B-2440 Geel, Belgium), 2,4-dihydroxyquinoline (from Chemos GmbH, Germany), 2,6-dihydroxyquinoline (from ABCR GmbH & Co. KG, Germany), and 2,8-dihydroxyquinoline (from Chemos GmbH, Germany). Examples of difunctional monoamino compounds (with two active hydrogens that can substitute) suitable for use as the second linker include, for example, (all available from Aldrich) 3-amino-9-ethylcarbazole, 3-amino-2-methoxydibenzofuran, 8-amino-6-methoxyquinoline hydrobromide, 3-aminoquinoline, 5-aminoquinoline, 6-aminoquinoline, 4-aminoquinaldine, 9-aminoacridine hydrochloride hydrate, 4-amino-2,1,3-benzothiadiazole, 2-amino-2,1,3-benzothiadiazole, 1-aminobenzotriazole, 6-aminobenzotriazole, 2-amino-3-bromo-5-methylpyridine, 2-amino-5-bromo-3-methylpyridine, 6-amino-3-bromo-2-methyl pyridine, 2-amino-4-(bromophenyl) thiazole, 2-amino-5-bromopyridine, 2-amino-6-bromopyridine, 2-amino-5-bromopyrimidine, 2-amino-5-tert-butyl-1,3,4-thiadiazole, 2-amino-4-chlorobenzothiazole, 2-amino-5-chlorobenzoxazole, 2-amino-4-(4-chlorophenyl) thiazole, and 2-amino-5-(ethylthio)-1,3,4-thiadiazole. Examples of di-amino compounds suitable for use as the second linker include, for example, (all available from Aldrich) 3,6-diaminoacridine hydrochloride, 2,3-diamino-5-bromopyridine, 3,8-diamino-6-phenylphenanthridine, 2,6-diaminopyridine, 3,4-diaminopyridine, 2,4-diaminopyrimidine, and 4,5-diaminopyrimidine.

The particular reaction conditions for bonding the first linker with the hydrazone and with the second linker can be selected by a person of ordinary skill in the art based on the particular reaction involved and the discussion herein. Appropriate conditions for the reaction of epichlorohydrin as the first linker with various hydrazones is described in detail in the Examples. In particular, the synthesis and characterization of compounds 2–5 are described in detail in the Examples.

Organophotoreceptor (OPR) Preparation Methods

Following conventional terminology, the number of layers in the OPR refers to the layers with charge transport compounds and/or charge generating compounds. Thus, the presence of overlayers, underlayers, release layers and the like do not alter the single layer versus dual layer terminology.

Positive Inverted Dual Layer OPR

A positive polarity, inverted dual layer organic photoreceptor can be prepared by incorporating a charge transfer compound disclosed herein into the charge transport layer and then over-coating this layer with a charge generation solution to form a charge generation layer. The positive inverted dual layer is designed to operate with a positive surface charge that is discharge upon illumination at the point of illumination. An example of a specific approach for forming this structure is presented below.

In one embodiment, a charge transport solution comprising a 1:1 ratio by weight of a charge transfer compound as described herein to a binder, such as polycarbonate Z binder (commercially available from Mitsubishi Gas Chemical under the trade name Lupilon™ Z-200 resin), can be prepared by combining a solution of 1.25 g of one of the charge transfer compounds as described herein in 8.0 g of tetrahydrofuran with 1.25 g of polycarbonate Z in 6.25 g of tetrahydrofuran. The charge transport solution can be hand-coated onto a 76-micrometer (3-mil) thick aluminized polyester substrate (such as a Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 51-micrometer (2-mil) orifice between the blade and polyester, can be used to prepare a film with an 8–10-micron thickness after drying the wet film in an oven at 110° C. for 5–10 min.

A dispersion for forming a charge generation layer can be prepared by micronising 76.1 g of oxytitanium phthalocyanine pigment (H.W. Sands Corp., Jupiter, Fla.), 32.6 g of S-Lec B Bx-5 polyvinylbutyral resin (Sekisui Chemical Co. Ltd.), and 641.3 g of methyl ethyl ketone, using a horizontal sand mill operating in recycle mode for 8 hours. After milling, the charge generation layer base can be diluted with methyl ethyl ketone to decrease the total solids of the solution to 4.0 wt %. The charge generation solution can be hand-coated onto the charge transport layer using a knife coater, set to a 20–25 micron (0.8–1.0 mil) orifice between the blade and charge transfer layer to prepare a sub-micron thick charge generation layer (CGL) film after drying the wet film in an oven at 110° C. for 3–5 min.

Negative Dual Layer OPR

A negative polarity, dual layer organic photoreceptor can be prepared forming a charge generation layer and then incorporating a charge transfer compound disclosed herein into a solution and coating this solution over the charge generation layer to form a charge transfer layer. A negative dual layer is designed to operate with a negative surface charge that is discharged upon illumination at the point of illumination. A specific example for forming a negative dual layer is described below.

In one embodiment, a charge generation layer mill-base dispersion can be prepared by micronizing 76.1 g of oxytitanium phthalocyanine pigment, 32.6 g of S-Lec B Bx-5 polyvinylbutyral resin (Sekisui Chemical Co. Ltd.), and 641.3 g of methyl ethyl ketone, using a horizontal sand mill operating in recycle mode for 8 hours. Following milling the charge generating layer base can be diluted with methyl ethyl ketone to decrease the total solids of the solution to 4.0 wt %. The charge generation solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 20–25 micron (0.8–1.0 mil) orifice between the blade and substrate, can be used to prepare the sub-micron thick charge generating layer film after drying the wet film in an oven at 110° C. for 3–5 min.

A charge transport solution comprising a 1:1 ratio by weight of a charge transfer compound described herein to polycarbonate Z binder is prepared by combining a solution of 1.25 g of the charge transfer compound in 8.0 g of tetrahydrofuran with 1.25 g of polycarbonate Z in 6.25 g of tetrahydrofuran. A knife coater, set to a 51-micrometer (2-mil) orifice between the blade and polyester, can be used to prepare an 8–10-micron thick film after drying the wet film in an oven at 110° C. for 5–10 min.

Single Layer OPR

A single layer organic photoreceptor can be prepared by incorporating a charge transfer compound disclosed herein along with a charge generating composition into a single coating solution and then coating this solution over a suitable substrate. A single layer OPR is designed to operate with a surface charge, which may be positive or negative, that is discharged upon illumination at the point of illumination in which the charge is generated in a layer and transported through that layer.

In practice, single layer OPRs are used predominantly with positive surface charges. In general, through the photoconductive and semiconductive materials of interest, electrons have a significantly lower mobility than holes. With low concentrations of charge generating pigment compounds to limit charge trapping in a single layer structure, the electron-hole pairs can be generated some distance from the surface of the OPR after light is absorbed. However, the electron-hole pairs still tend to be closer to the surface than the substrate, such that the electron has less distance to travel than the hole in a positive single layer OPR. The hole from the electron-hole pair can transport through the remaining portion of the OPR to the underlying substrate. Thus, while electrons may travel some distance to neutralize positive charges at the surface of a positively charged OPR, the electrons would still have significantly larger distance to travel to the substrate in a negative single layer OPR. For single layer embodiments, it can be desirable to include an optional electron transport compound to facilitate the electron transport.

However, the use of a dual layer positive OPR is complicated by the formation of a thin charge generating layer over a charge transport layer due to processing complications of dip coating and solvent selection. Also, the thin charge generating layer can be abraded away in use without a good overcoat layer. Thus, a single layer positive OPR may offer some advantages over a positive dual layer system. Since the formation of negative dual layer OPRs do not have the complications of positive dual layer OPRs and since limited electron mobility hinders operation of negative single layer OPRs, negative single layer OPRs generally are less desirable although they are within the scope of the present disclosure for incorporation of the improved charge transport compounds described herein.

In one embodiment especially for the preparation of a single layer OPR, a charge transport pre-mix solution containing a 1:1 ratio by weight of a charge transport compound disclosed herein to polycarbonate Z binder can be prepared by combining a solution of 1.25 g of the charge transfer compound in 8.0 g of tetrahydrofuran with 1.25 g of polycarbonate Z in 6.25 g of tetrahydrofuran. A charge generating layer mill-base dispersion can be prepared by micronizing 76.1 g of oxytitanium phthalocyanine pigment, 32.6 g of polycarbonate Z binder resin, and 641.3 g of tetrahydrofuran, using a horizontal sand mill operating in pass mode for 6–8 passes. An electron transport pre-mix solution containing a 1:1.4 ratio of (4-n-butoxycarbonyl-9-fluorenylidene) malononitrile electron transport compound to Polycarbonate Z binder can be prepared by combining a solution of 1.25 g of one of the electron transporting material in 8.0 g of tetrahydrofuran with 1.75 g of polycarbonate Z in 9 g of tetrahydrofuran.

The single layer coating solution can be prepared by combining 14 g of the charge transport pre-mix, 4.08 g of the electron transport premix and 1.92 g of the charge generating layer mill-base dispersion. The single layer solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 50–75 micron (2–3 mil) orifice between the blade and substrate, can be used to prepare a single layer film with an 8–10 micron thickness after drying the wet film in an oven at 110° C. for 5–10 min.

The invention will now be described further by way of the following examples.

EXAMPLES

Example 1

Preparation of Epoxy-Derivitized Hydrazones

This example presents the synthesis of four epoxy-derivatized hydrazones. These hydrazones can be reacted with a linker compound to form charge transfer compounds as described herein.

Preparation of 9-Ethyl-3-carbazolecarboxaldehyde N-2,3-epoxypropyl-N-phenylhydrazone A mixture of 9-ethyl-3-carbazolecarboxaldehyde phenylhydrazone (3.1 g, 0.01 mol), 85% powdered potassium hydroxide (2.0g, 0.03 mol) and anhydrous potassium carbonate (~5 g) in 25 ml of epichlorohydrin was stirred vigorously at 55–60° C. for 1.5–2 h. The course of the reaction was monitored using thin layer chromatography on silica gel 60 F254 plates (commercially obtained from Merck) using a 1:4 volume per volume mixture of acetone and hexane as the eluant. After termination of the reaction, the mixture was cooled to room temperature, diluted with ether and washed with water until the wash water was neutral in pH. The organic layer was dried over anhydrous magnesium sulfate, treated with activated charcoal, and filtered. Ether was removed, and the residue was dissolved in the mixture of toluene and 2-propanol in 1:1 ratio by volume. The crystals formed upon standing were filtered off, and washed with 2-propanol to give 3.0 g (81.2%) of 9-ethyl-3-carbazolecarboxaldehyde N-2,3-epoxypropyl-N-phenylhydrazone. The solid product had a melting point (m.p.) of 136–137° C. after being recrystallized from a mixture of toluene and 2-propanol in 1:1 ratio by volume. A $^1$H-NMR spectrum of 9-ethyl-3-carbazolecarboxaldehyde N-2,3-epoxypropyl-N-phenylhydrazone was obtained in $CDCl_3$ with a 250 MHz NMR. The peaks were found at (ppm) $\delta=8.35$ (s, 1H, 4-$H_{Ht}$); $\delta=8.14$ (d, J=7.8 Hz, 1H, 1-$H_{Ht}$); $\delta=7.93$ (d, J=7.6 Hz, 1H, 2-$H_{Ht}$); $\delta=7.90$ (s, 1H, CH=N); $\delta=7.54–7.20$ (m, 8H, Ph, Ht); $\delta=6.96$ (t, J=7.2 Hz, 1H, 4-$H_{Ph}$); $\delta=4.37$ (m, 3H, $CH_2CH_3$, one of the $NCH_2$ protons); $\delta=4.04$ (dd, $J_1=4.3$ Hz, $J_2=16.4$ Hz, 1H, next of the $NCH_2$ protons); $\delta=3.32$ (m, 1H, CH); $\delta=2.88$ (dd, 1H, part of the ABX system, cis-$H_A$ of $CH_2O$, $J_{AX}=2.6$ Hz, $J_{AB}=4.9$ Hz); $\delta=2.69$ (dd, 1H, part of the ABX system, trans-$H_B$ of $CH_2O$, $J_{BX}=4.0$ Hz); $\delta=1.44$ (t, J=7.2 Hz, 3H, $CH_3$). An elemental analysis found the following weight percents of the elements: C, 78.32; H, 6.41; N, 11.55, which compares with the following calculated elemental weight percent for a compound with the formula $C_{24}H_{23}N_3O$: C, 78.02; H, 6.28; N, 11.37.

Preparation of 4-(Diphenylamino)benzaldehyde N-2,3-epoxypropyl-N-phenylhydrazone 4-(Diphenylamino)benzaldehyde N-2,3-epoxypropyl-N-phenylhydrazone was prepared according to the preparation procedure above for 9-ethyl-3-carbazolecarbaldehyde N-2,3-epoxypropyl-N-phenylhydrazone except that 9-ethyl-3-carbazolecarbaldehyde phenylhydrazone was replaced with 4-(diphenylamino) benzaldehyde phenylhydrazone (3.5g, 0.01 mol). The yield of 4-(diphenylamino) benzaldehyde N-2,3-epoxypropyl-N-phenylhydrazone was 3.0 g (71.4%). The melting point (m.p.) of the product was 141–142.5° C. after being recrystallized from toluene. A $^1$H-NMR spectrum of 4-(diphenylamino) benzaldehyde N-2,3-epoxypropyl-N-phenylhydrazone was obtained in $CDCl_3$ with a 250 MHz NMR. The peaks were found at (ppm) $\delta=7.65–6.98$ (m, 19H, CH=N, Ar); $\delta=6.93$ (t, J=7.2 Hz, 1H, 4-$H_{Ph}$); $\delta=4.35$ (dd, 1H, part of the ABX system, one of $NCH_2$ protons, $J_{AX}=2.4$ Hz, $J_{AB}=16.4$); $\delta=3.99$ (dd, 1H, part of the ABX system, other of $NCH_2$ protons, $J_{BX}=4.1$ Hz); $\delta=3.26$ (m, 1H, CH); $\delta=2.84$ (dd, 1H, part of the ABX system, cis-$H_A$ of $CH_2O$, $J_{AX}=2.7$ Hz, $J_{AB}=4.8$ Hz); $\delta=2.62$ (dd, 1H, part of the ABX system, trans-$H_B$ of $CH_2O$, $J_{BX}=4.1$ Hz). An elemental analysis found the following weight percents of the elements: C, 80.02; H, 6.31; N, 9.91, which compares with the following calculated elemental weight percent for a compound with the formula $C_{28}H_{25}N_3O$ of: C, 80.16; H, 6.01; N, 10.02.

Preparation of 4-(Diethylamino)benzaldehyde N-2,3-epoxypropyl-N-phenylhydrazone 4-(Diethylamino)benzaldehyde N-2,3-epoxypropyl-N-phenylhydrazone was prepared according to the preparation procedure above for 9-ethyl-3-carbazolecarboxaldehyde N-2,3-epoxypropyl-N-phenylhydrazone except that 9-ethyl-3-carbazolecarboxaldehyde phenylhydrazone was replaced by 4-(diethylamino)benzaldehyde phenylhydrazone and the product was recrystallized from diethyl ether. The yield of 4-(diethylamino)benzaldehyde N-2,3-epoxypropyl-N-phenylhydrazone was 69%. The product had a melting point of 79–80.5° C. when recrystallized from diethyl ether. A $^1$H-NMR spectrum was obtained in $CDCl_3$ with the following results ($\delta$ in ppm, 250 MHz): $\delta=7.7–6.7$ (m, 8H, Ar, CH=N); $\delta=6.6$ (d, 2H, 2-H, 6-H of p-Ph); $\delta=4.4–3.6$ (m, 2H, $NCH_2CH$); $\delta=3.6–3.0$ (m, 5H, $CH_2CH_3$, $CH_2CHCH_2$); $\delta=2.75$ (m, 1H, ABX, cis-$H_A$ of $CH_2O$); $\delta=2.55$ (m, ABX, trans-$H_B$ of $CH_2O$); $\delta=1.1$ (t, J=7.0 Hz, 6H, $CH_3$). An elemental analysis found the following weight percents of the elements: C, 74.45; H, 7.84; N, 12.72, which compares with the following calculated elemental weight percent for a compound with the formula $C_{20}H_{25}N_3O$ of: C, 74.27; H, 7.79; N, 12.99.

Preparation of 4-(4,4'-dimethyldiphenylamino)benzaldehyde N-2,3-epoxypropyl-N-phenylhydrazone A mixture of 4-(4,4'-dimethyldiphenylamino)benzaldehyde phenylhydrazone (3.9 g, 0.01 mole), 85% powdered potassium hydroxide (2.0 g, 0.03 mole) and anhydrous potassium carbonate in 25 ml of epichlorohydrin was stirred vigorously at 55–60° C. for 1.5–2 hours. The course of the reaction was monitored using thin layer chromatography on silica gel 60 F254 plates (commercially available from Merck, Whitehouse Station, N.J.) using 1:4 v/v mixture of acetone and hexane as eluant. After termination of the reaction, the mixture was cooled to room temperature, diluted with ether, and washed with water until the wash water had a neutral pH. The organic layer was dried over anhydrous magnesium sulfate, treated with activated charcoal, and filtered. Ether was evaporated, and the residue was purified by crystallization from toluene. The final product obtained by further purification by column chromatography (silica gel Merck grade 9385, 60 Å, Aldrich; 4:1 v/v solution of hexane and acetone as the eluent). The yield of 4-(4,4'-Dimethyldiphenylamino)benzaldehyde N-2,3-epoxypropyl-N-phenylhydrazone was 65.5%. The product was characterized with $^1$H-NMR in CDCl$_3$ (400MHz instrument) with peaks observed at the following delta values in ppm: 7.62 (s, 1H), 7.55–6.90 (m, 17H); 4.35 (dd, 1H), 3.98 (dd, 1H), 3.27 (m, 1H), 2.85 (dd, 1H), 2.63 (dd, 1H); 2.32 (s, 6H). An elemental analysis yielded the following results in weight percent: % C=80.42, % H=6.41, % N=9.21, which compares with calculated values for C$_{30}$H$_{29}$N$_3$O of % C=80.51, % H=6.53, % N=9.39.

Example 2

Preparation of Charge Transport Compounds

This examples describes the synthesis of four charge transport compounds corresponding to compounds 2–5 above.

Preparation of Compound 2

A. 1.9 ml (13.5 mmol) quantity of triethylamine (TEA) was slowly added to a solution of 9-ethyl-3-carbazolecarboxaldexyde N-2,3-epoxypropyl-N-phenylhydrazone (10.0 g, 27.1 mmol, as synthesized as described in Example 1) and 2,5-dimercapto-1,3,4-thiadiazole (2.03 g, 13.55 mmol) in 15 ml of 2-butanone, while the temperature of the reaction mixture was maintained below 30° C. The reaction mixture was stored overnight at room temperature. The crystals that formed upon standing for 24 h were filtered off and washed with 2-propanol to give a yield of 10.1 g (84.1%) of product hydrazone. The product had a melting point of 167–170.5° C. (recrystallized from toluene). A $^1$H-NMR spectrum was obtained for the product (250 MHz, CDCl$_3$) which yielded the following values, δ in ppm, J, (Hz): 8.25 (2H, s, 4-H Ht); 8.12 (2H, d, J=7.8 Hz, 1-H Ht); 7.83 (2H, d, J=7.8 Hz, 2-H Ht); 7.81 (2H, s, CH=N); 7.50–7.14 (16H, m, Ht, Ar); 6.99 (2H, t, J=7.0 Hz, 4-H Ph); 4.44 (2H, m, CH); 4.27 (4H, q, J=6.8 Hz, C$\underline{H}_2$CH$_3$); 4.06–3.82 (6H, m, OH, NCH$_2$); 3.58 (2H, m, H$_A$, double set of signals of AB part of ABX system, CH$_2$S); 3.34 (2H, m, H$_B$, double set of signals of AB part of ABX system, CH$_2$S); 1.37 (6H, t, J=6.8 Hz, CH$_2$C$\underline{H}_3$). The infrared absorption spectrum was as follows: ν in cm$^{-1}$: 3368 (OH, br); 3048 (CH$_{arom}$); 2972, 2930 (CH$_{aliph}$); 806, 747, 730, 694 (CH=CH of carbazole, monosubstituted benzene). An elemental analysis of the product yielded the following in weight %: C, 67.39; H, 5.38; N, 12.72, which compared with a calculated elemental distribution in weight percent for C$_{50}$H$_{48}$N$_8$O$_2$S$_3$ of: C, 67.54; H, 5.44; N, 12.60.

Preparation of Compound 3

Compound 3 was prepared and isolated as described for Compound 2, except that 4-(diethylamino)benzaldehyde N-2,3-epoxypropyl-N-phenylhydrazone (8.7 g, 27.1 mmol, prepared as described in Example 1) was used instead of 9-ethyl-3-carbazolecarboxaldexyde N-2,3-epoxypropyl-N-phenylhydrazone. The yield of Compound 3 was 7.6 g (70.4%). The product had a melting point of 114.5–116° C. (recrystallized from toluene). A $^1$H-NMR spectrum was obtained for the product (250 MHz, DMSO-d$_6$) yielded the following values, δ in ppm, J, (Hz): 7.74 (2H, s, CH=N); 7.48–7.14 (12H, m, Ar); 6.80 (2H, t, J=7.1 Hz, 4-H Ph); 6.64 (4H, d, J=8.7 Hz, p-Ph); 5.54 (2H, d, J=3.9 Hz, OH); 4.20–3.90 (6H, m, NCH$_2$CH); 3.30 (8H, q, J=6.9 Hz, C$\underline{H}_2$CH$_3$); 3.18 (4H, m, CH$_2$S); 1.06 (12H, t, J=7.1 Hz, CH$_2$C$\underline{H}_3$). An infrared absorption spectrum yielded the following results, ν in cm$^{-1}$: 3324 (OH, br); 3019 (CH$_{arom}$); 2968, 2927, 2957 (CH$_{aliph}$); 813, 749, 694 (mono- and p-disubstituted benzene). An elemental analysis of the product yielded the following results in weight %: C, 63.11; H, 6.46; N, 14.20, which compared with a calculated elemental distribution in weight % for C$_{42}$H$_{52}$N$_8$O$_2$S$_3$ of: C, 63.28; H, 6.58; N, 14.06.

Preparation of Compound 4

Compound 4 was prepared as described for Compound 2 except that 4-(diphenylamino)benzaldehyde N-2,3-epoxypropyl-N-phenylhydrazone (11.2 g, 27.1 mmol, prepared as described in Example 1) was used instead of 9-ethyl-3-carbazolearboxaldexyde N-2,3-epoxypropyl-N-phenyl-hydrazone. The product was isolated by subjecting the reaction mixture to chromatography using propanone/hexane (1:4) as the eluant. After removal of the eluants, the residue was recrystallized from toluene. Compound 4 was filtered off and washed with 2-propanol. The reaction resulted in a yield of 8.9 g (66.4%). The product had a melting point of 165–167° C. (recrystallized from toluene). The product had an $^1$H-NMR spectrum (400 MHz, CDCl$_3$) as follows, δ in ppm, J, (Hz): 7.61 (2H, s, CH=N); 7.53 (4H, d, J=8.8 Hz, Ar); 7.40–6.97 (34H, m, Ar); 4.47 (2H, m, CH); 4.08–3.90 (6H, m, NCH$_2$, OH); 3.61 (2H, ddd, J$_{AB}$=14.1 Hz, J$_{AX}$=6.6 Hz, H$_A$ of SCH$_2$); 3.37 (2H, dd, J$_{BX}$=7.1 Hz, H$_B$ from SCH$_2$). An infrared absorption spectrum of the product yielded the following spectral peaks, wavenumbers, ν, in cm$^{-1}$: 3384 (OH, br); 3060, 3033 (CH$_{arom}$); 2914 (CH$_{aliph}$); 827, 752, 695 (mono- and p-disubstituted benzene). An elemental analysis of the product yielded the following results in weight %: C, 70.33; H, 5.28; N, 11.41, which compared with a calculated elemental distribution in weight % for C$_{58}$H$_{52}$N$_8$O$_2$S$_3$ of: C, 70.42; H, 5.30; N, 11.33.

Preparation of Compound 5

Compound 5 was prepared as described for Compound 2, except that 4-(4,4'-dimethyldiphenylamino)benzaldehyde N-2,3-epoxypropyl-N-phenylhydrazone (12.1 g, 27.1 mmol, prepared as described in Example 1) was used instead of 9-ethyl-3-carbazolearboxaldexyde N-2,3-epoxypropyl-N-phenylhydrazone. The product was isolated according to the procedure described for Compound 4. The yield of product was 9.6 g (68.1%). A $^1$H-NMR spectrum of the product (400 MHz, CDCl$_3$) yielded the following, δ in ppm, J, (Hz): 7.60 (2H, s, CH=N); 7.49 (4H, d, J=8.2 Hz, Ar); 7.39–7.29 (8H, m, Ar); 7.08–6.96 (22H, m, Ar); 4.46 (2H, m, CH); 4.03 (2H, d, J=3.8 Hz, OH); 4.02 (2H, dd, J$_{AB}$=15.0 Hz, J$_{AX}$=5.1 Hz, H$_A$ of NCH$_2$); 3.96 (2H, dd, J$_{BX}$=7.0 Hz, H$_B$ of NCH$_2$); 3.60 (2H, dd, J$_{AB}$=14.3 Hz, J$_{AX}$=3.7 Hz, H$_A$ of SCH$_2$); 3.37 (2H, dd, J$_{BX}$=7.3 Hz, H$_B$ from SCH$_2$); 2.29 (12H, s, 4-CH$_3$). An infrared absorption spectrum yielded spectral peaks as follows, wavenumbers, ν, in cm$^{-1}$: 3355 (OH, br); 3024 (CH$_{arom}$); 2919, 2858 (CH$_{aliph}$); 815, 750, 693 (CH=CH of mono- and p-disubstituted benzene). An elemental analysis of the product yielded in weight %: C, 71.17; H, 7.69; N, 10.81, which compared with a calculated elemental distribution in weight % for C$_{62}$H$_{60}$N$_8$O$_2$S$_3$ of: C, 71.23; H, 7.79; N, 10.72.

Example 3

Ionization Potential

This example provides ionization potential measurements for the four charge transport compounds described in Example 2.

Samples for ionization potential (Ip) measurements were prepared by dissolving the compound under testing in tetrahydrofuran. The solution was hand-coated on an aluminized polyester substrate that was precision coated with a methylcellulose-based adhesion sub-layer to form a charge transport material (CTM) layer. The role of the sub-layer was to improve adhesion of the CTM layer, to retard crystallization of charge transport compound, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of the sub-layer and CTM layer each was ~0.4 µm. No binder material was used with CTM in the preparation of the samples for Ip measurements.

The ionization potential $I_P$ of the samples was measured by the method described in Daskeviciene et al., "Derivatives of 2,5-dimercapto-1,3,4-thiadiazole as hole transporting material", Lithuanian Journal of Physics, 2001, 41, No. 4–6, pp. 521–526, incorporated herein by reference. The ionization potential measurements for the four charge transport compounds in Example 2 are summarized in Table 1.

Example 4

Charge Carrier Mobility

This example presents measurements of charge carrier mobility for samples prepared from the four charge transport compounds of Example 2.

Samples for the charge carrier mobility measurement were prepared in two ways, without binder or with binder. Samples without binder were prepared similarly to the samples for the ionization potential testing except the thickness of the CTM layer was 7–9 µm. Samples with a binder were prepared as follows. A mixture of 0.1 g of the charge transport compound and 0.1 g of polyvinylbutyral (S-LEC B BX-1, commercially obtained from Sekisui) was dissolved in 2 ml of tetrahydrofuran (THF). The solution was coated on the polyester film with conductive Al layer by the dip roller method. After drying for 1 h at 80° C., a clear ~10 µm thick layer was formed.

The hole drift mobility was determined as described in "Investigation of charge carrier transfer in electrophotographic layers of chalkogenide glasses," Proceedings IPCS 1994: The Physics and Chemistry of Imaging Systems, Rochester, N.Y., pp 747–752, which is hereby incorporated by reference. Positive corona charging created an electric field inside the CTM layer at various initial surface potentials, U. The charge carriers were generated at the layer surface by illumination with pulses of nitrogen laser (pulse duration was 2 ns, wavelength 337 nm). The layer surface potential decreased, as a result of pulse illumination, by up to 1–5% of initial potential before illumination. The capacitance probe that was connected to the wide frequency band electrometer measured the rate of change in the surface potential, dU/dt. The transit time $t_t$ was determined by the change (kink) in the curve of the dU/dt transient on a linear or double logarithmic scale. The drift mobility was calculated by the formula $\mu=d^2/U_0 \cdot t_t$, where d is the layer thickness and $U_0$ is the surface potential at the moment of illumination. The mobility field dependence on the initial surface potential may be approximated by the function:

$$\mu=\mu_0 e^{\alpha\sqrt{E}}$$

where E is the electric field strength in the layer, $\mu_0$ is the zero field mobility, and α is Pool-Frenkel parameter characterizing mobility field dependence.

The mobility characterizing parameters $\mu_0$ and α values as well as the mobility value at the $6.4\times10^5$ V/cm field strength are given in Table 1.

TABLE 1

| Sample | $\mu_0$, (cm²/V · s) | $\mu$, (cm²/V · s) | α, (cm/V)$^{0.5}$ | $I_p$, (eV) |
|---|---|---|---|---|
| Compound 2 | $7.5 \cdot 10^{-8}$ | $2.8 \cdot 10^{-5}$ | 0.0075 | 5.31 |
| Compound 3 | $3.1 \cdot 10^{-8}$ | $1.5 \cdot 10^{-5}$ | 0.0077 | 5.08 |
| Compound 3 + PVB, 1:1 by weight | $1.3 \cdot 10^{-9}$ | $1.7 \cdot 10^{-7}$ | 0.0061 | — |
| Compound 4 | $7.0 \cdot 10^{-7}$ | $7.2 \cdot 10^{-5}$ | 0.0057 | 5.25 |
| Compound 5 | $2.6 \cdot 10^{-6}$ | $1.3 \cdot 10^{-4}$ | 0.0049 | 5.15 |
| Compound 5 + PVB, 1:1 by weight | $1.5 \cdot 10^{-8}$ | $1.1 \cdot 10^{-6}$ | 0.0055 | — |

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising:
   (a) a charge transport compound having the formula

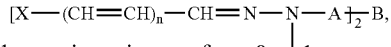

where n is an integer from 0 to 4;
   X is an (N,N-disubstituted)arylamine group;
   Ar is an aryl group or a heterocyclic group;
   A is a first linking group with the formula —(CH$_2$)$_p$— which can be branched or linear, where p is an integer from 3 to 20 inclusive and where one or more methylene groups can be optionally replaced by O, S, a carbonyl group, urethane, urea, an ester group, a —NR$_{16}$ group, a CHR$_{17}$ group, or a CR$_{18}$R$_{19}$ group where R$_{16}$, R$_{17}$, R$_{18}$ and R$_{19}$ are, independently, H, hydroxyl, thiol, an amine group, an alkyl group, an alkaryl group, an aryl group, or part of a ring; and
   B is a second linking group having the formula -Q-Z-Q'-, where Q and Q' are, independently, O, S or NR$_1$, where R$_1$ is an H, an alkyl group, an alkaryl group or an aryl group, and Z comprises a heterocyclic group;
   (b) a charge generating compound; and
   (c) an electrically conductive substrate over which the charge transport compound and the charge generating compound are located.

2. An organophotoreceptor according to claim 1 wherein said organophotoreceptor is in the form of a flexible belt.

3. An organophotoreceptor according to claim 1 wherein said organophotoreceptor is in the form of a drum.

4. An organophotoreceptor according to claim 1 wherein said organoreceptor further comprises an electron transport compound.

5. An organophotoreceptor according to claim 1 comprising:
   (a) a charge transport layer comprising said charge transport compound and a polymeric binder; and
   (b) a charge generating layer comprising said charge generating compound and a polymeric binder.

6. An organophotoreceptor according to claim 1 wherein said charge transport compound is selected from the group consisting of the following formulas:

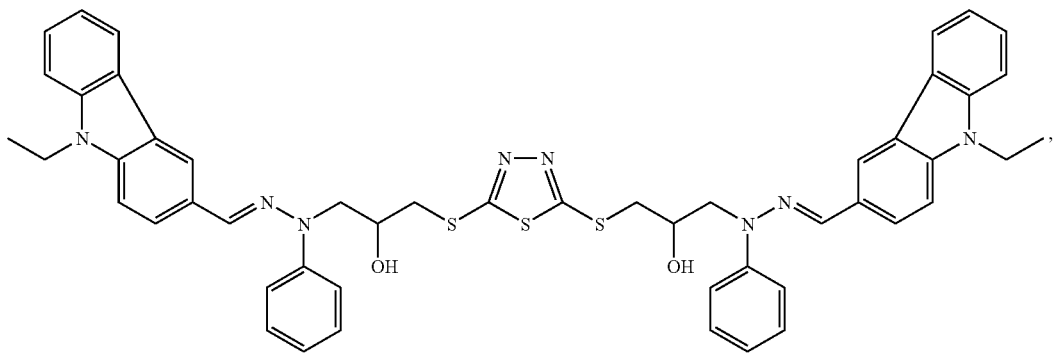
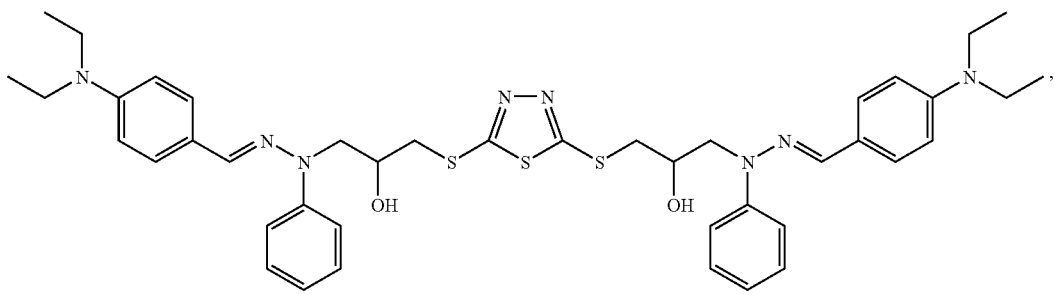
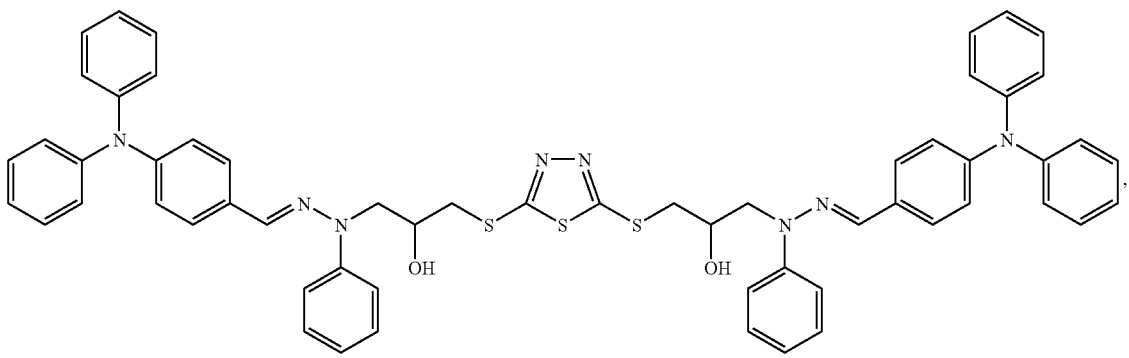
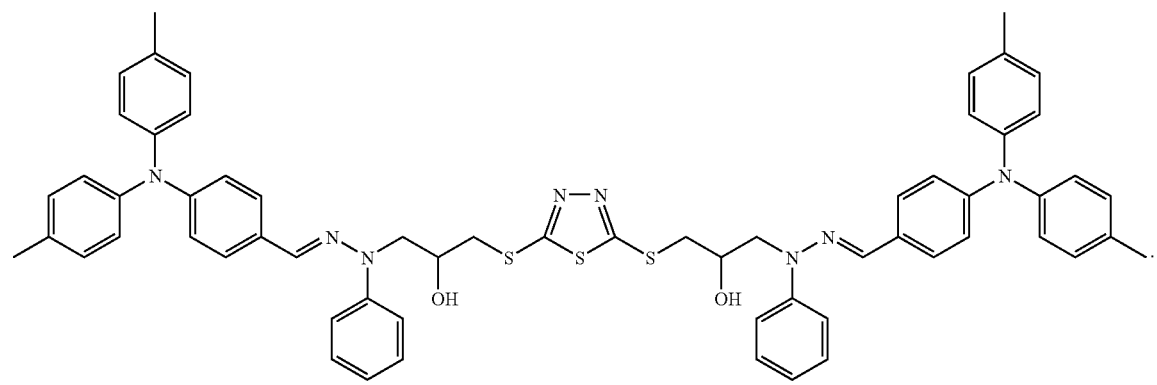

7. An electrophotographic imaging apparatus comprising:
(a) a plurality of support rollers; and
(b) an organophotoreceptor operably coupled to said support rollers with motion of said support rollers resulting in motion of said organophotoreceptor, said organophotoreceptor comprising:
(i) a charge transport compound having the formula

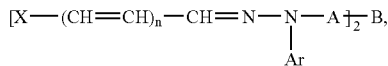

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group;
(ii) a charge generating compound; and
(iii) an electrically conductive substrate over which said charge transport compound and said charge generating compound are located.

8. An electrographic imaging apparatus according to claim 7 wherein said organophotoreceptor further comprises an electron transport compound.

9. An electrophotographic imaging apparatus according to claim 7 wherein said electrophotographic imaging apparatus further comprises a liquid toner dispenser.

10. A charge transport compound having the formula

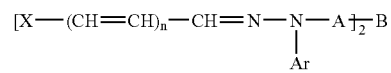

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{16}$ group, a $CHR_{17}$ group, or a $CR_{18}R_{19}$ group where $R_{16}$, $R_{17}$, $R_{18}$ and $R_{19}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$, where $R_1$ is an H, an alkyl group, an alkaryl group or an aryl group, and Z comprises a heterocyclic group.

11. A charge transport compound according to claim 10 wherein said charge transport compound is selected from the group consisting of the following formulas:

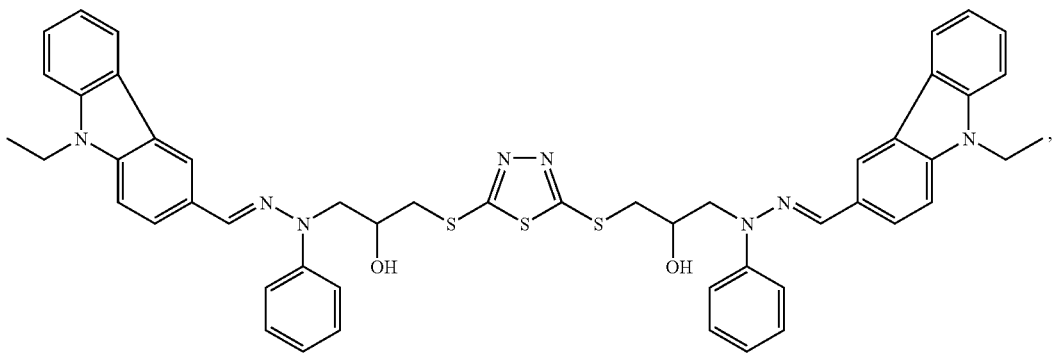

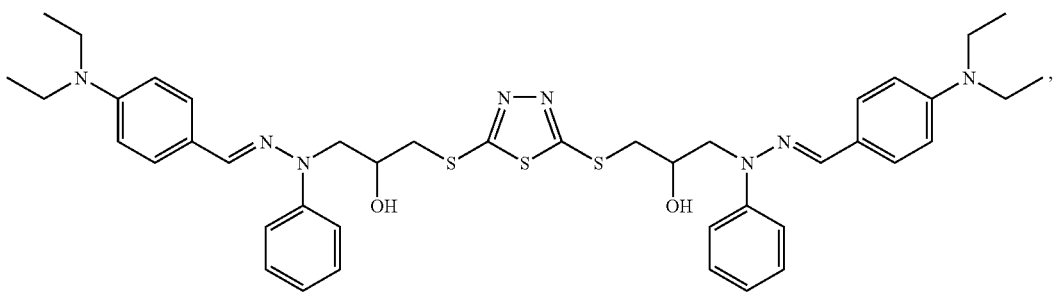

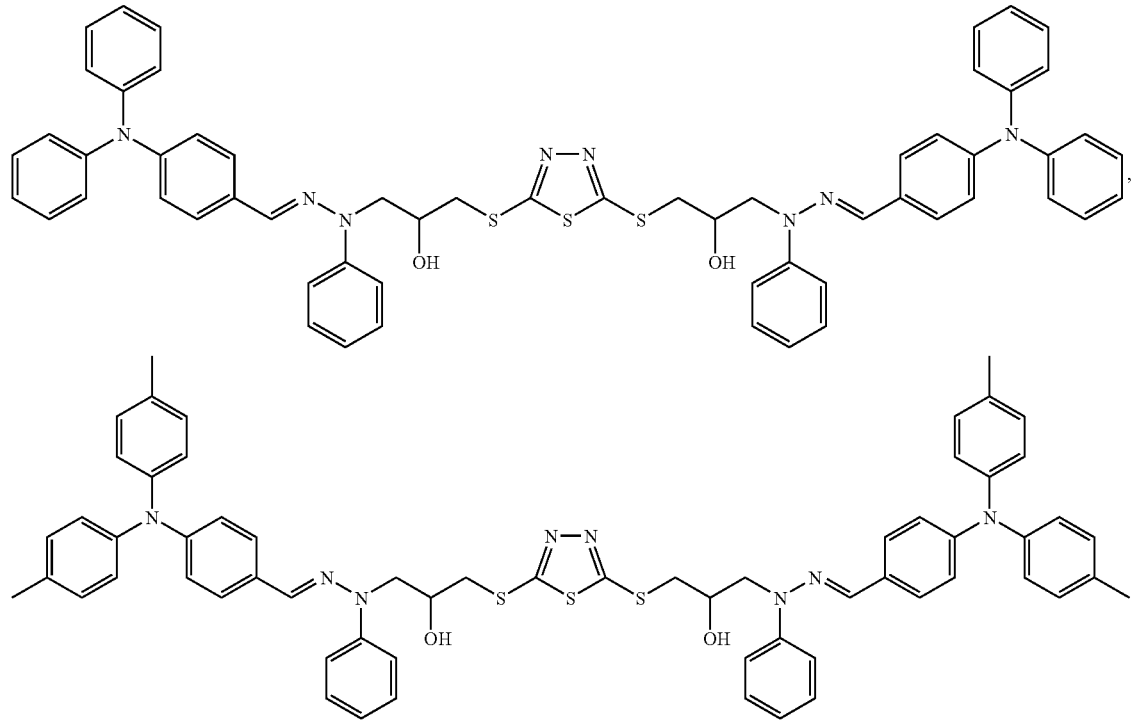

12. A charge transport compound according to claim 10 wherein first linker A comprises —CH$_2$CHOHCH$_2$—.

13. A charge transport compound according to claim 10 wherein X of said charge transport compound comprises a julolidine group.

14. A charge transport compound according to claim 10 wherein X of said charge transport compound comprises a triphenylamine group.

15. A charge transport compound according to claim 10 wherein X of said charge transport compound comprises a carbozole group.

16. A charge transport compound according to claim 10 wherein n=0.

17. A charge transport compound according to claim 10 wherein Q=Q'=S.

18. A charge transport compound according to claim 10 wherein Q=Q'=S and Z comprises a heterocyclic group comprising sulfur.

* * * * *